(12) United States Patent
Dallman et al.

(10) Patent No.: US 6,923,519 B2
(45) Date of Patent: Aug. 2, 2005

(54) BLOOD BAG SUPPORT STRUCTURE AND METHOD FOR REFRIGERATORS

(75) Inventors: Brian L. Dallman, Weaverville, NC (US); Harry D. Wall, Asheville, NC (US); Joseph E. Revis, Jr., Weaverville, NC (US); Henry Meinken, Jr., Weaverville, NC (US)

(73) Assignee: GSLE Development Corp., Charlotte, NC (US)

( * ) Notice: Subject to any disclaimer, the term of this patent is extended or adjusted under 35 U.S.C. 154(b) by 0 days.

(21) Appl. No.: 10/000,352

(22) Filed: Dec. 4, 2001

(65) Prior Publication Data

US 2003/0102788 A1 Jun. 5, 2003

(51) Int. Cl.[7] .............................................. A47B 96/04
(52) U.S. Cl. ................... 312/408; 312/410; 312/330.1; 108/108; 211/187
(58) Field of Search .......................... 312/228.1, 330.1, 312/311, 408, 410, 350, 351; 108/106–109, 147.17; 211/90.03, 103, 106, 181.1, 187, 94.01

(56) References Cited

U.S. PATENT DOCUMENTS

| | | | | |
|---|---|---|---|---|
| 2,815,649 A | * | 12/1957 | Di Angelus et al. | 312/408 |
| 3,844,416 A | * | 10/1974 | Potter | 211/162 |
| 3,984,163 A | * | 10/1976 | Boorman et al. | 312/408 |
| 4,138,175 A | * | 2/1979 | Tattershall | 312/408 |
| 4,735,470 A | * | 4/1988 | Falk | 312/408 |
| 5,303,997 A | * | 4/1994 | Kropf | 312/334.4 |
| 5,441,338 A | * | 8/1995 | Kane et al. | 312/408 |
| 5,486,046 A | * | 1/1996 | Jernstrom et al. | 312/408 |
| 5,735,589 A | * | 4/1998 | Herrmann et al. | 312/408 |
| 5,893,620 A | * | 4/1999 | Birgelis | 312/408 |
| 6,227,636 B1 | * | 5/2001 | Lye et al. | 312/408 |
| 6,302,036 B1 | * | 10/2001 | Carson et al. | 108/147.17 |
| 6,311,856 B2 | * | 11/2001 | Battaglia et al. | 108/107 |
| 6,345,795 B1 | * | 2/2002 | Bartz, Jr. | 211/187 |
| 6,364,136 B1 | * | 4/2002 | Weshler et al. | 312/408 |

FOREIGN PATENT DOCUMENTS

| | | | | | |
|---|---|---|---|---|---|
| DE | DT 2007791 | * | 8/1971 | | 312/351 |
| JP | 2000014468 | * | 1/2000 | | |

* cited by examiner

*Primary Examiner*—Lanna Mai
*Assistant Examiner*—Hanh V. Tran
(74) *Attorney, Agent, or Firm*—Baker & Hostetler LLP

(57) ABSTRACT

An apparatus for supporting an item in a refrigerator housing has a frame having rails arranged for the items. A plurality of slotted strips and/or a drawer slide guide are mounted to the housing. A plurality of brackets are provided for engaging the slotted strips and/or drawer slide guide supporting the frame.

8 Claims, 4 Drawing Sheets

BLOOD BAG SUPPORT STRUCTURE AND METHOD FOR REFRIGERATORS

FIELD OF THE INVENTION

The present invention relates generally to a support structure and method for supporting items in refrigerators. More particularly, the present invention relates to supporting items such as blood bags or leukocyte bags in refrigerators.

BACKGROUND OF THE INVENTION

It has been known to store blood in plastic bags in refrigerators, such as in the blood bank industry or in the case of leukocyte filtration. Presently, blood bags are sometimes stored on shelves which are slidably or fixedly mounted by drawer slides to the sides of a cabinet. It is sometimes desirable to hang anywhere from one to a large number of bags upright in the refrigerator. In the case of leukocyte bags, it is desirable to hang the leukocyte bags in the refrigerator from rails near the top of the cabinet, which drain through a tube to a filter and then into another bag in a drawer or at the bottom of the cabinet itself, which receives the filtered leukocyte.

It has also been known to suspend the bags from rails that are permanently fastened to the top or sides of the refrigerator cabinet top or sides. However, these systems are not easily converted to different heights and/or configurations, and it would be desirable to be able to have a configuration in a refrigerator that is easily height-adjustable and/or convertible between sliding shelves on a hanging rack.

Moreover, it would also be desirable to be able to easily adapt or reconfigure the arrangement inside a refrigerator cabinet between various configurations as needed. A disadvantage of present systems is that it is difficult to modify existing cabinets to accept new rails. For example, if drawer guides and/or pilaster strips for supporting shelves are to be moved or added into a cabinet (such as for example in an AABB temperature-specified 4-degrees C. cabinet) it is necessary to drill holes in the cabinet. Such drilling can generally only be performed by a sophisticated installer who knows where the electrical items and other components such as the copper refrigeration tubing are located within the cabinet walls so that damage to these components can be avoided. It would be desirable to be able to more commercially adapt a refrigerator to different configurations using existing drawer guides and/or pilaster strips.

Accordingly, there is a need for an apparatus and method for conveniently providing and/or reconfiguring a support structure for supporting blood bags and/or leukocyte bags in refrigerator cabinets.

SUMMARY OF THE INVENTION

The present invention provides a convenient apparatus and method for providing and/or reconfiguring a support structure for supporting blood bags and/or leukocyte bags in a refrigerator cabinet. The same embodiments the invention also provides an apparatus for a refrigerator that is easily height-adjustable and/or convertible between sliding shelves and hanging racks.

In one aspect, the invention pertains to an apparatus for supporting an item in a refrigerator housing, comprising a frame having rails arranged for the items to be suspended therefrom; a plurality of slotted strips mounted to the housing; and a plurality of brackets, each for engaging the slotted strips and supporting the frame.

In another aspect, the invention pertains to an apparatus for supporting an item in a refrigerator, comprising a frame having rails arranged for the items to be suspended therefrom; means for supporting the frame; and means for height adjustably mounting the supporting means to the housing.

In still another aspect, the invention pertains to a method for supporting an item in a refrigerator housing, comprising the steps of installing a plurality of brackets on the inside of the housing; and placing a frame on the brackets to be supported by the brackets.

There has thus been outlined, rather broadly, the more important features of the invention in order that the detailed description thereof that follows may be better understood and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

Figure 1:
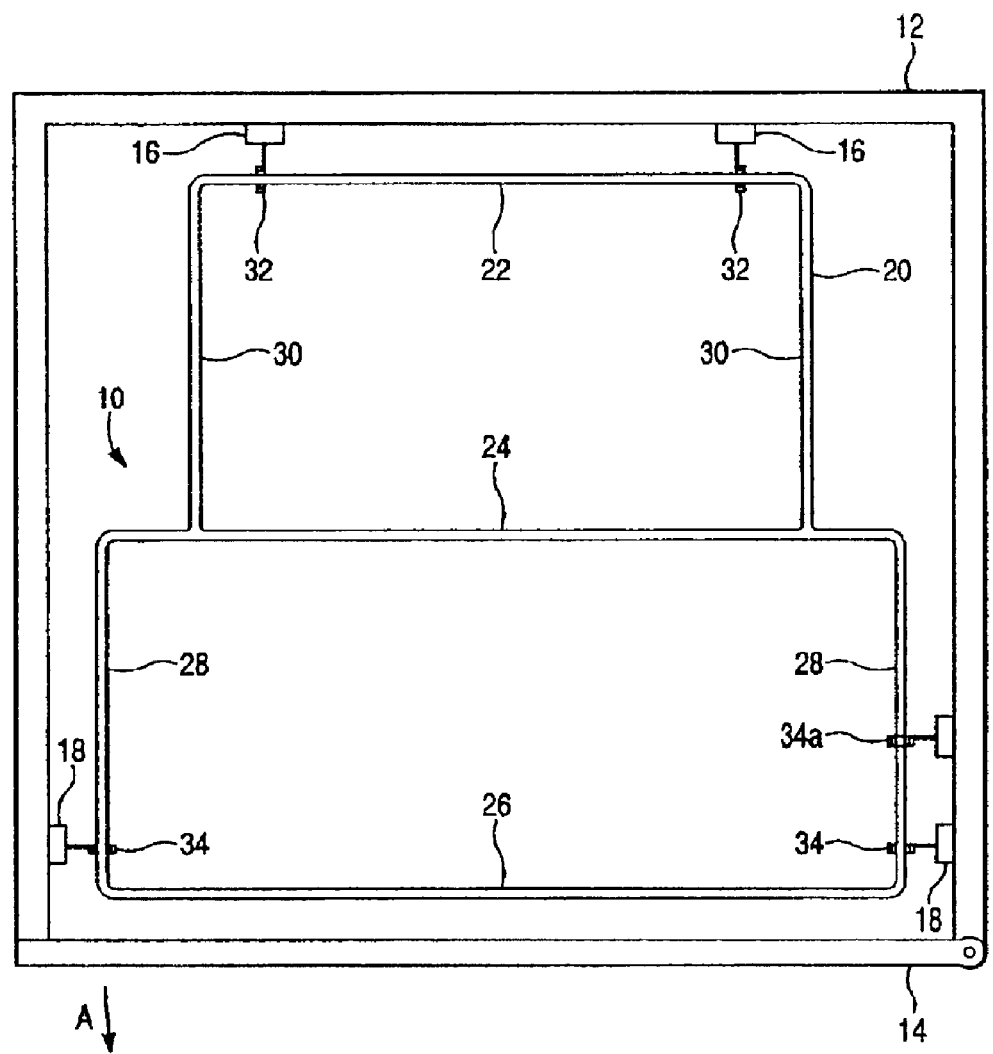
FIG. 1 is a top plan view showing a blood bag support frame installed in a refrigerator cabinet, according to a first embodiment of the invention.

The present invention provides an apparatus and method for supporting items such as blood bags and/or leukocyte bags in a refrigerator cabinet. Preferred embodiments of the invention and variations thereof are described in the accompanying drawings, in which like reference numerals indicate like elements.

Figure 2:
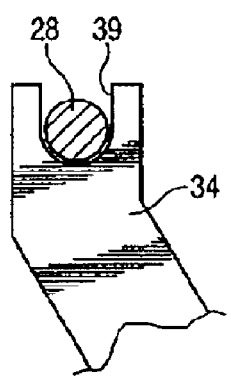
FIG. 2 is a detail view showing the interaction of a support member with a support frame.
Figure 3:
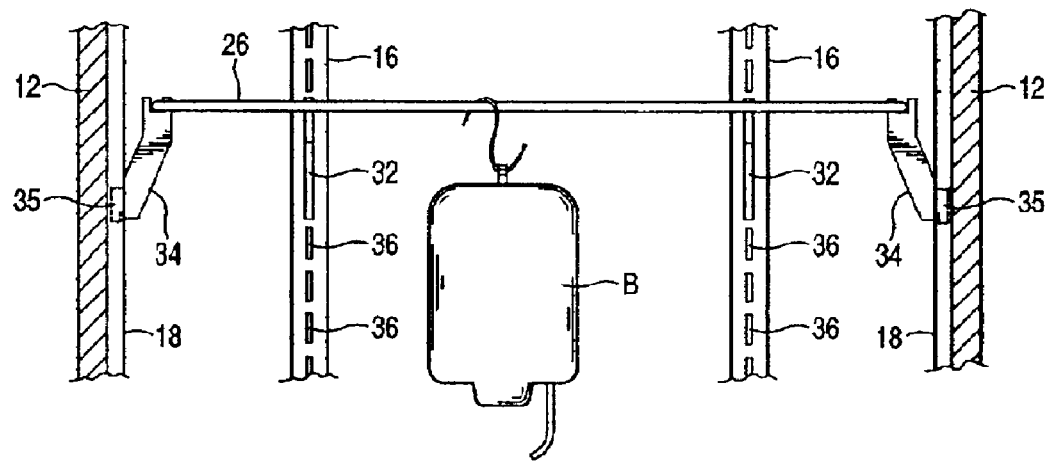
FIG. 3 is a cutaway plan view the embodiment of FIG. 1.

FIGS. 1 through 4 illustrate a first embodiment 10 of the invention. In this embodiment 10, a refrigerator cabinet housing 12 having a swinging door 14 includes mounted on the inner surfaces of the refrigerator housing 12 a rear pair of pilaster strips 16 mounted to a back wall and a front pair of pilaster strips 18 mounted to opposing side walls. These pilaster strips 16 and 18 can be mounted on the refrigerator housing when it is manufactured, or may be retrofitted later. The arrow A indicates a direction of opening of the door 14. A framework 20 is provided on which an item such as a blood bag or a leukocyte bag B is supported as shown in FIG. 3.

Returning to FIGS. 1 through 4, a benefit of some embodiments of the invention is the ability of the bag support framework 20 to be adjustably mounted to pilaster strips 16 and 18 at different locations on the framework 20. By virtue of this, the pilaster strips 16 and 18 can be mounted on the housing 12 where they will not interfere with components inside the refrigerator housing 12.

Figure 4:
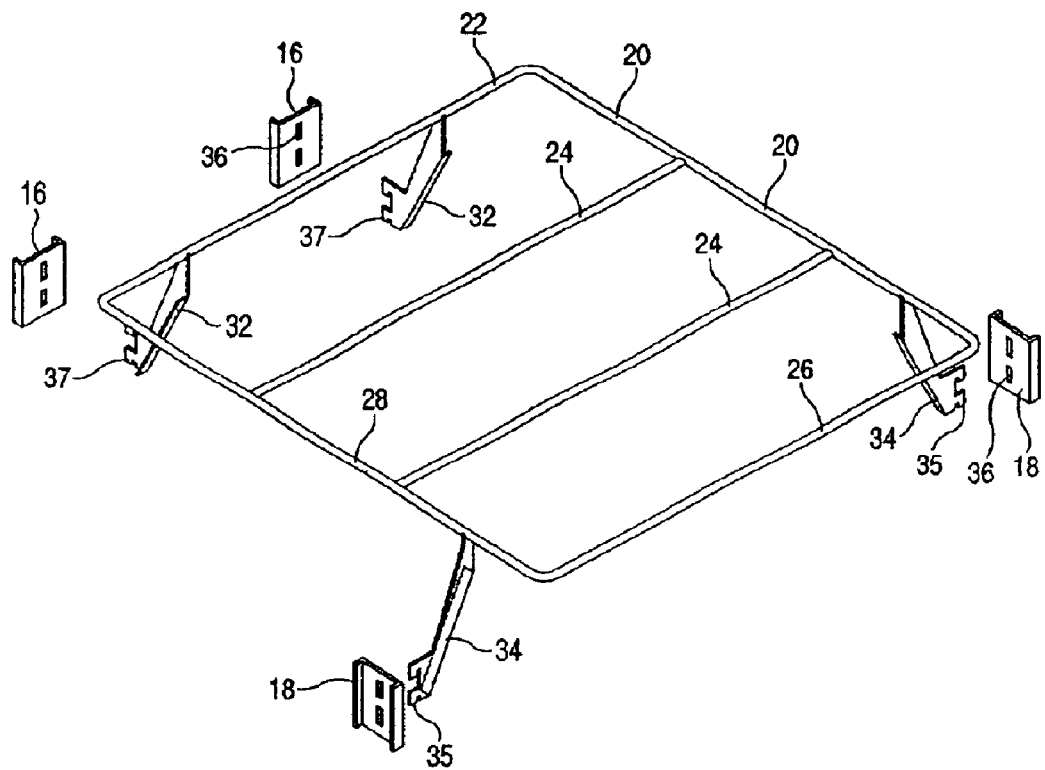
FIG. 4 is a partially exploded perspective view of a variation of the embodiment of FIG. 1.

As shown in FIG. 1, the blood bag supporting framework 20 includes a rear rail 22, a central rail 24, and a front rail 26, which are connected to two front side rails 28 and to rear side rails 30 as shown. FIGS. 1 and 4 show two possible arrangements for a framework 20 that can support blood bags, that have different outlines and a different number of crossbars or transverse rails. FIGS. 1 and 4 therefore show two different variations of the first embodiment, with regard to the arrangement of the side rails 28, 30 and the transverse rails 22, 24 and 26. In FIG. 1, there are three transverse rails 22, 24 and 26, and the rear side rails 30 are spaced apart by a lesser width than the front side rails 28. However, any suitable framework arrangement may be utilized, including any number of transverse rails, and any outline shape of the rails. For example it may be desirable to shape the outline of the rails to provide a clearance around any internal components in the refrigerator. By way of example, in the embodiment of FIG. 4, there are four transverse rails, labeled as 22, 24, and 26. Two side rails 28 are provided which extend the entire length of the framework 20. The support frame 20 is supported on two rear brackets 32 and two front brackets 34. The brackets 34 have one or more tongues 35 that project from the bottom of the brackets and engage slots 36 in the pilaster strips 18. Similarly, brackets 32 have one or more tongues 37 projecting from a lower part thereof that engage with slots 36 in the pilaster strips 16.

As seen in FIG. 2, the upper portion of each bracket 32 and 34 includes a U-shaped channel 39 which is sized to receive the cross-section of the portion of the framework 20 being supported (in the example of FIG. 2 the side rail 28 is being supported). Accordingly, FIGS. 1 and 2 illustrate an embodiment where the framework 20 is supported on the brackets 32 and 34 merely by resting in U-shaped channels on the brackets 32 and 34. This arrangement provides several advantages. First, the framework 20 can be lifted up and conveniently removed from the brackets 32 and 34. This makes the arrangement easy to install and adjust, because the framework 20 may be removed, and each bracket 32 and 34 may be appropriately positioned individually on a respective strip 16, 18 before the framework is then lowered on the brackets 32 and 34.

Also, in this embodiment, the brackets 32 and 34 may engage with the framework 20 at any location along with the outer rails. Thus, as illustrated in phantom lines at 34A, the bracket 34 may be positioned anywhere along the side rails 28 to accommodate different locations of the pilaster strip 18. The outer brackets 32 and 34 are similarly adjustable in location across the width of the framework 20 to accommodate different placements of the strips 16.

The embodiment of FIG. 4 may also utilize the interaction of the brackets 32 and 34 with the frame 20 that is shown in FIG. 2. However, in all versions of the invention, including those of FIGS. 1 and 2, it is possible to attach the brackets 32 and 34 to the framework 20 by any other suitable attachment method, including fixedly welding or otherwise affixing the brackets 32 and or 34 to the framework 20. If the brackets 32 and/or 34 are fixedly attached to the framework 10, it is desirable to provide enough flexibility in the arrangement so that the brackets 32 and 34 can be deflected as necessary during installation to permit the tongues 35 and 37 to engage the slots 36.

The embodiments of FIGS. 1 through 4 are therefore suitable for use where pilaster strips 16 and 18, having slots 36 are installed in a refrigerator housing 12. The pilaster strips 16 and 18 may already be present in the interior of the refrigerator housing, or may be added as desired. Although the preferred embodiment shows tongues 35 and 37 engaging slots 36, any other suitable type of connection may be used. Further, although a number of slots are shown in order to provide height adjustment, the invention is also suitable for use where only a single height mounting point is provided. This can be a single slot, or any other mounting device such as for example a projecting pin, rib, or a groove.

Figure 5:
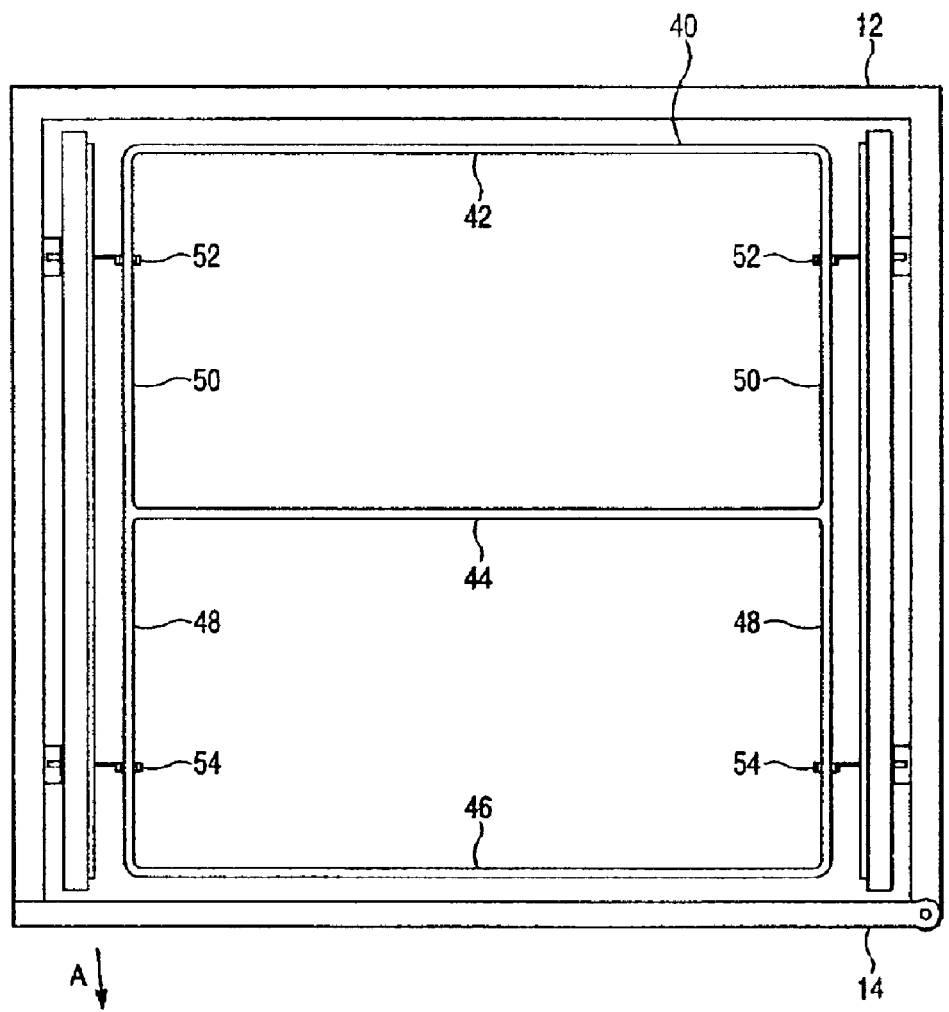
FIG. 5 is a top plan view of a second embodiment of the present invention, showing a blood bank support frame mounted on drawer slides in a refrigerator cabinet.
Figure 6:
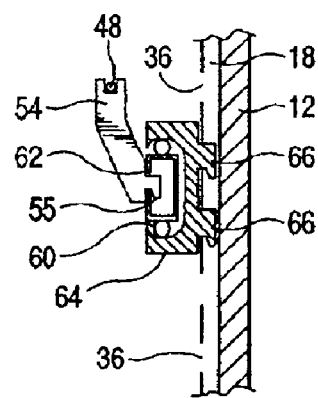
FIG. 6 is a cutaway detail view showing the interaction of a support frame, support bracket, and drawer slide according to the embodiment of FIG. 5.
Figure 7:
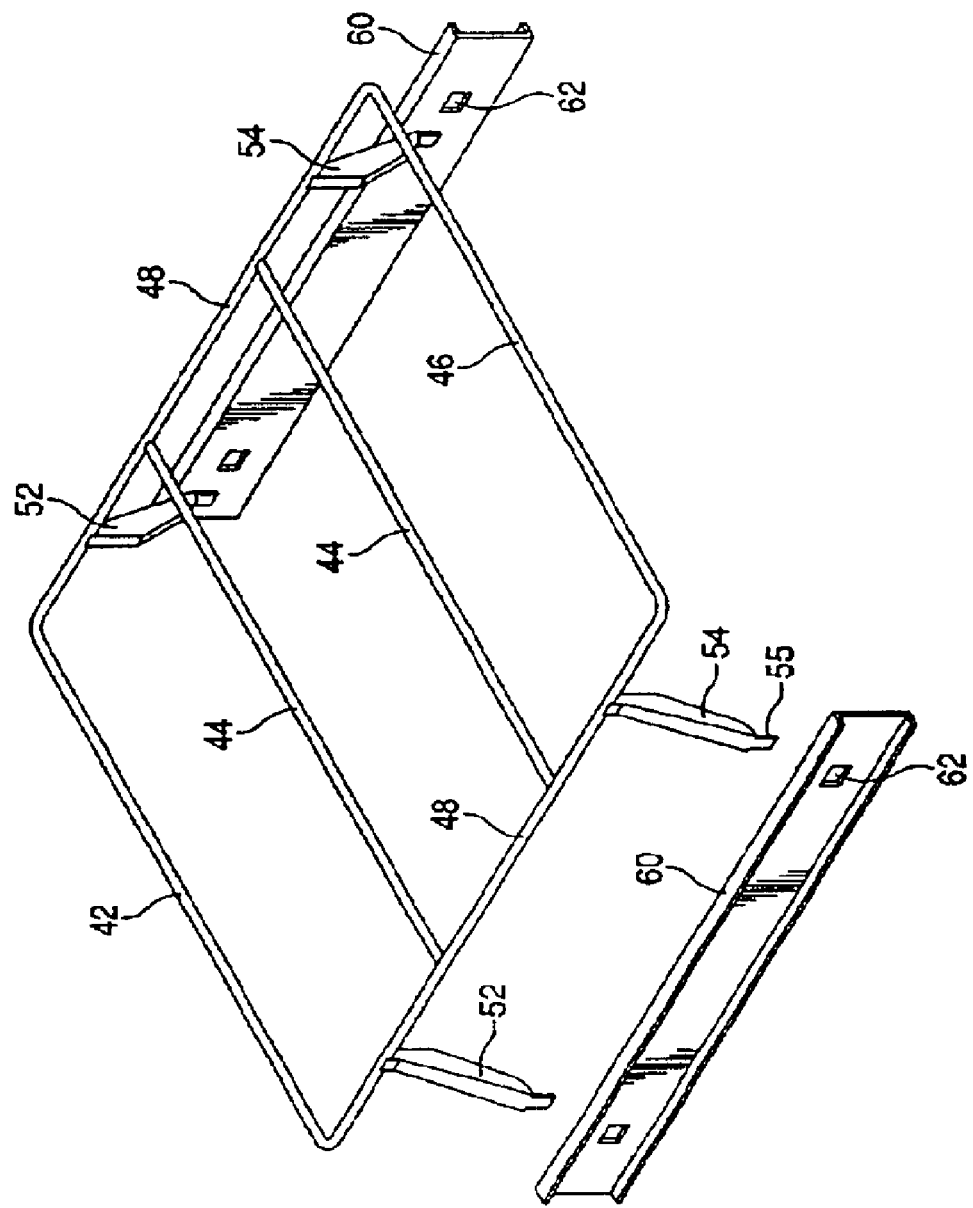
FIG. 7 is a partially exploded perspective view of the embodiment of FIG. 5.

Turning now to the embodiment shown in FIGS. 5 through 7, another embodiment is shown which incorporates the use of sliding drawer guides. In some refrigerators, the sliding drawer guides may already be present on the interior of the cabinet to support sliding shelves. In these situations, it is possible to remove the existing shelf, and instead insert the arrangement shown in FIG. 7 in place of the shelf that has been removed.

As shown in FIGS. 5 through 7, the second embodiment includes a frame 40 having a rear transverse rail 42, a transverse rail 44, and front transverse rail 46. Side rails 48 and 50 are provided and are supported by brackets 52 and 54. The brackets 52 and 54 can support the frame 40 as illustrated in FIG. 2, or may be fixedly attached, for example by being welded, as has been discussed above.

FIG. 6 shows a bracket 54 having a tongue 55 that extends into a slot 62 of a drawer slide element 60. The drawer slide element 60 is supported by bearings in a drawer slide guide 64. The drawer slide guide 64 may be fixedly mounted to the side of the refrigerator housing 12, or as shown in FIG. 6 may include tongues 56 that project into slots 36 on a pilaster strip 18. Although a ball bearing-type sliding drawer slide and guide arrangement is shown, other drawer mounting arrangements such as a simple lip or groove on the interior cabinet wall can be employed.

It will be appreciated that the connection between the bracket 54 and drawer slide 60 may be fixed or removable, and that the slide guide 64 may also be fixed or removably attached to the housing 12. The use of removable connections in particular provides easy disassembly, and in the version shown in FIG. 6 the feature of height adjustment as well. Also, it is possible for the refrigerator housing 12 to have pilaster strips 16 and 18 which can accommodate the embodiments of FIGS. 1 through 4 and/or the embodiments of FIGS. 5 through 7 without modification to the strips. Further, a combination of multiple support frames 20 can be installed at various heights, and a conventional sliding shelf can also be used together with one or more frameworks 20 to create various combinations of frameworks 20, and/or shelves as desired.

The many features and advantages of the invention are apparent from the detailed specification, and thus, it is intended by the appended claims to cover all such features and advantages of the invention which fall within the true spirits and cope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for supporting an item in a refrigerator cabinet, comprising:
   a frame having rails arranged for the item to be suspended therefrom;
   a plurality of slotted strips adapted to be vertically mounted in the cabinet; and
   a plurality of brackets, wherein each bracket is mounted proximal the slotted strips and supports the frame, wherein the brackets each have a first end, and wherein the first end has a generally upwardly facing U-shaped channel that receives and supports the frame and wherein the frame has peripheral rails, and wherein channels and rails are sized so that only the channels support the rails at more than one point along the peripheral rails wherein the brackets each have a second end that is mounted within a slide, a slide guide mounted to the slotted strips, wherein the slide moves along the slide guide.

2. An apparatus according to claim 1, further comprising an item wherein the item is a blood bag.

3. An apparatus according to claim 1, wherein the frame has a plurality of generally parallel transverse rails.

4. An apparatus according to claim 1, wherein the slide guide are height adjustably mounted to the slotted strips.

5. An apparatus for supporting an item in a refrigerator cabinet, comprising:
   means for suspending the item;
   means for supporting the suspending means; and
   means for height adjustably mounting the supporting means to a housing, wherein the supporting means comprises a bracket having a first end with a generally U-shaped channel that receives and supports the suspending means, and a second end a, wherein a frame has peripheral rails, and wherein channels and rails are sized so that only the channels support the rails at more than one point along the peripheral rails, wherein the second end of the supporting means is mounted within a slide, a slide guide mounted to the mounting means, wherein the slide guide slidably supports the slide.

6. An apparatus according to claim 5, further comprising an item, wherein the item is a blood bag.

7. An apparatus according to claim 5, wherein the slide guide is height adjustably mounted to the mounting means.

8. An apparatus according to claim 5, wherein the frame includes a plurality of transverse rails.

\* \* \* \* \*